(12) United States Patent
Perschbacher et al.

(10) Patent No.: US 7,844,332 B2
(45) Date of Patent: Nov. 30, 2010

(54) ATRIOVENTRICULAR DELAY ADJUSTMENT ENHANCING VENTRICULAR TACHYARRHYTHMIA DETECTION

(75) Inventors: David L. Perschbacher, Coon Rapids, MN (US); Kenneth L. Baker, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 558 days.

(21) Appl. No.: 11/676,464

(22) Filed: Feb. 19, 2007

(65) Prior Publication Data

US 2007/0142869 A1 Jun. 21, 2007

Related U.S. Application Data

(63) Continuation-in-part of application No. 10/274,697, filed on Oct. 18, 2002, now Pat. No. 7,376,461.

(51) Int. Cl.
*A61N 1/365* (2006.01)
(52) U.S. Cl. .............................. 607/14; 607/9
(58) Field of Classification Search .................. 607/9, 607/14
See application file for complete search history.

(56) References Cited

U.S. PATENT DOCUMENTS

| 4,059,116 A | 11/1977 | Adams |
| 4,208,008 A | 6/1980 | Smith |
| RE30,387 E | 8/1980 | Denniston, III et al. |
| 4,432,360 A | 2/1984 | Mumford et al. |
| 4,503,857 A | 3/1985 | Boute et al. |
| 4,712,556 A | 12/1987 | Baker, Jr. |
| 4,860,749 A | 8/1989 | Lehmann |
| 4,928,688 A | 5/1990 | Mower |
| 4,941,471 A | 7/1990 | Mehra |
| 4,944,298 A | 7/1990 | Sholder |
| 4,972,834 A | 11/1990 | Begemann et al. |

(Continued)

FOREIGN PATENT DOCUMENTS

EP 0033418 8/1981

(Continued)

OTHER PUBLICATIONS

"U.S. Appl. No. 10/274,697, Non-Final Office Action mailed Jul. 9, 2007", 5 pgs.

(Continued)

*Primary Examiner*—Michael Kahelin
(74) *Attorney, Agent, or Firm*—Schwegman, Lundberg & Woessner, P.A.

(57) ABSTRACT

This document discusses, among other things, an apparatus comprising an atrial sensing circuit, a ventricular sensing circuit and an atrioventricular (AV) delay adjustment circuit. The atrial sensing circuit detects a first fast atrial pace that concludes a timing interval that is shorter than or equal to a first threshold value. The ventricular sensing circuit detects a first condition that comprises a sensed intrinsic first fast ventricular contraction that occurs within a specified first period of a most recently detected first fast atrial pace. The fast ventricular contraction concludes a timing interval that is shorter than or equal to a second threshold value. The AV delay adjustment circuit attempts to decrease an AV delay at least in part in response to detecting the first condition. Other apparatuses and methods are disclosed.

34 Claims, 10 Drawing Sheets

U.S. PATENT DOCUMENTS

| | | | |
|---|---|---|---|
| 4,998,974 A | 3/1991 | Aker | |
| 5,129,394 A | 7/1992 | Mehra | |
| 5,183,040 A | 2/1993 | Nappholz et al. | |
| 5,331,966 A | 7/1994 | Bennett et al. | |
| 5,334,220 A | 8/1994 | Sholder | |
| 5,356,425 A | 10/1994 | Bardy et al. | |
| 5,360,437 A | 11/1994 | Thompson | |
| 5,365,932 A | 11/1994 | Greenhut | |
| 5,379,776 A * | 1/1995 | Murphy et al. | 600/518 |
| 5,417,714 A | 5/1995 | Levine et al. | |
| 5,462,060 A | 10/1995 | Jacobson et al. | |
| 5,523,942 A | 6/1996 | Tyler et al. | |
| 5,549,649 A | 8/1996 | Florio et al. | |
| 5,560,369 A | 10/1996 | McClure et al. | |
| 5,560,370 A | 10/1996 | Verrier et al. | |
| 5,607,460 A | 3/1997 | Kroll et al. | |
| 5,620,471 A | 4/1997 | Duncan | |
| 5,620,473 A | 4/1997 | Poore | |
| 5,626,623 A | 5/1997 | Kieval et al. | |
| 5,653,738 A | 8/1997 | Sholder | |
| 5,690,689 A | 11/1997 | Sholder | |
| 5,700,283 A | 12/1997 | Salo | |
| 5,702,424 A | 12/1997 | Legay et al. | |
| 5,713,930 A | 2/1998 | van der Veen et al. | |
| 5,713,932 A | 2/1998 | Gillberg et al. | |
| 5,716,382 A | 2/1998 | Snell | |
| 5,724,985 A | 3/1998 | Snell et al. | |
| 5,725,559 A | 3/1998 | Alt et al. | |
| 5,730,141 A | 3/1998 | Fain et al. | |
| 5,738,096 A | 4/1998 | Ben-Haim | |
| 5,741,308 A | 4/1998 | Sholder | |
| 5,749,906 A | 5/1998 | Kieval et al. | |
| 5,776,167 A | 7/1998 | Levine et al. | |
| 5,782,887 A | 7/1998 | van Krieken et al. | |
| 5,788,717 A | 8/1998 | Mann et al. | |
| 5,792,193 A | 8/1998 | Stoop | |
| 5,792,200 A | 8/1998 | Brewer | |
| 5,800,464 A | 9/1998 | Kieval | |
| 5,800,471 A | 9/1998 | Baumann | |
| 5,814,077 A | 9/1998 | Sholder et al. | |
| 5,814,081 A | 9/1998 | Ayers et al. | |
| 5,836,987 A | 11/1998 | Baumann et al. | |
| 5,840,079 A | 11/1998 | Warman et al. | |
| 5,861,007 A | 1/1999 | Hess et al. | |
| 5,873,895 A | 2/1999 | Sholder et al. | |
| 5,873,897 A | 2/1999 | Armstrong et al. | |
| 5,893,882 A | 4/1999 | Peterson et al. | |
| 5,897,575 A | 4/1999 | Wickham | |
| 5,931,856 A | 8/1999 | Bouhour et al. | |
| 5,935,081 A | 8/1999 | Kadhiresan | |
| 5,944,744 A | 8/1999 | Paul et al. | |
| 5,978,710 A | 11/1999 | Prutchi et al. | |
| 5,983,138 A | 11/1999 | Kramer | |
| 6,026,320 A | 2/2000 | Carlson et al. | |
| 6,044,298 A | 3/2000 | Salo et al. | |
| 6,049,735 A | 4/2000 | Hartley et al. | |
| 6,052,620 A | 4/2000 | Gillberg et al. | |
| 6,081,747 A | 6/2000 | Levine et al. | |
| 6,088,618 A | 7/2000 | Kerver | |
| 6,091,988 A | 7/2000 | Warman et al. | |
| 6,122,545 A | 9/2000 | Struble et al. | |
| 6,128,533 A | 10/2000 | Florio et al. | |
| 6,151,524 A | 11/2000 | Krig et al. | |
| 6,233,485 B1 * | 5/2001 | Armstrong et al. | 607/14 |
| 6,246,909 B1 | 6/2001 | Ekwall | |
| 6,263,242 B1 | 7/2001 | Mika et al. | |
| 6,266,554 B1 | 7/2001 | Hsu et al. | |
| 6,292,693 B1 | 9/2001 | Darvish et al. | |
| 6,408,209 B1 | 6/2002 | Bouhour et al. | |
| 6,411,847 B1 | 6/2002 | Mower | |
| 6,421,564 B1 | 7/2002 | Yerich et al. | |
| 6,430,439 B1 | 8/2002 | Wentkowski et al. | |
| 6,434,424 B1 | 8/2002 | Igel et al. | |
| 6,438,421 B1 | 8/2002 | Stahmann et al. | |
| 6,484,058 B1 | 11/2002 | Williams et al. | |
| 6,501,988 B2 | 12/2002 | Kramer et al. | |
| 6,731,983 B2 | 5/2004 | Ericksen et al. | |
| 7,069,077 B2 | 6/2006 | Lovett et al. | |
| 7,142,915 B2 | 11/2006 | Kramer et al. | |
| 7,142,918 B2 | 11/2006 | Stahmann et al. | |
| 7,184,834 B1 | 2/2007 | Levine | |
| 7,283,872 B2 | 10/2007 | Boute et al. | |
| 7,376,461 B2 | 5/2008 | Perschbacher et al. | |
| 2001/0014817 A1 | 8/2001 | Armstrong et al. | |
| 2002/0120298 A1 | 8/2002 | Kramer et al. | |
| 2003/0069610 A1 | 4/2003 | Kramer et al. | |
| 2003/0078630 A1 | 4/2003 | Lovett et al. | |
| 2003/0233131 A1 | 12/2003 | Kramer et al. | |
| 2004/0010295 A1 | 1/2004 | Kramer et al. | |
| 2004/0077963 A1 | 4/2004 | Perschbacher et al. | |
| 2005/0283196 A1 | 12/2005 | Bocek et al. | |
| 2009/0149907 A1 | 6/2009 | Perschbacher et al. | |

FOREIGN PATENT DOCUMENTS

| | | |
|---|---|---|
| EP | 0360412 | 3/1990 |
| EP | 0401962 | 12/1990 |
| EP | 0597459 A2 | 5/1994 |
| EP | 0617980 | 10/1994 |
| EP | 0748638 | 12/1996 |
| EP | 1480715 B1 | 9/2009 |
| WO | WO-0071200 A1 | 11/2000 |
| WO | WO-0071202 A1 | 11/2000 |
| WO | WO-0071203 A1 | 11/2000 |

OTHER PUBLICATIONS

"U.S. Appl. No. 09/316,588, Non Final Office Action mailed Nov. 21, 2000", 4 pgs.

"U.S. Appl. No. 09/569,295, filed May 13, 2000", 30 pgs.

"U.S. Appl. No. 09/837,019, Non Final Office Action mailed Aug. 1, 2001", 5 pgs.

"French CNH Equipment Approvals", *Clinica*, 417, p. 9, (Sep. 5, 1990), 3 pgs.

"Pacemaker System Guide", (c) 2001 Guidant Corporation, 240 pgs.

"Rate-Adaptive Devices Impact Pacemaker Marker", *Clinica*, 467, p. 16, (Sep. 11, 1991), 6 pages.

Wittkampf, F.H.M., et al., "Rate Stabilization by Right Ventricular Patching in Patients with Atrial Fibrillation", *Pace*, 9, (Nov.-Dec. 1986), 1147-1153.

Zhu, D. W, "Electrophysiology, Pacing and Arrhythmia—Pacing Therapy for Atrial Tachyarrhythmias", *Clinical Cardiology*, 19(9), (1996), 737-742.

* cited by examiner

US 7,844,332 B2

ATRIOVENTRICULAR DELAY ADJUSTMENT ENHANCING VENTRICULAR TACHYARRHYTHMIA DETECTION

RELATED APPLICATIONS

This application is a Continuation-in-Part of U.S. application Ser. No. 10/274,697, filed Oct. 18, 2002 now U.S. Pat. No. 7,376,461, which is incorporated herein by reference.

TECHNICAL FIELD

This patent document pertains generally to cardiac rhythm or function management devices, and more particularly, but not by way of limitation, to atrioventricular delay adjustment enhancing ventricular tachyarrhythmia detection.

BACKGROUND

Cardiac rhythm or function management devices include implantable devices to help maintain heart rhythm or function. Such devices can include pacers, defibrillators, cardioverters, cardiac resynchronization therapy (CRT), or various combinations of such devices. Such devices can typically sense intrinsic heart contractions, deliver pacing pulses to evoke responsive heart contractions, or deliver a shock to interrupt certain arrhythmias. This can help improve the patient's heart rhythm or can help coordinate a spatial nature of the heart contraction, either of which may improve cardiac output of blood to help meet the patient's metabolic need for such cardiac output.

For example, detecting a ventricular tachyarrhythmia (e.g., a too-fast ventricular heart rhythm) often involves detecting a rate of ventricular heart contractions that exceeds a tachyarrhythmia rate threshold. By using multiple tachyarrhythmia rate thresholds, multiple tachyarrhythmia rate zones can be established, which can further classify different tachyarrhythmias based on which zone the heart rate falls within.

The present inventors have recognized that one problem with ventricular tachyarrhythmia detection is when an atrial pace is delivered at a heart rate that falls within one or more of the tachyarrhythmia rate zones. Such a "fast" atrial pace can inhibit detection of a tachyarrhythmic intrinsic ventricular contraction that occurs close in time to the fast atrial pace. This, in turn, can prevent proper diagnosis or treatment of a ventricular tachyarrhythmia. The present inventors have recognized an unmet need for improved apparatuses or methods for avoiding such problems.

OVERVIEW

This overview is intended to provide an overview of the subject matter of the present patent application. It is not intended to provide an exclusive or exhaustive explanation of the invention. The detailed description is included to provide further information about the subject matter of the present patent application.

This document describes devices and methods for enhancing detection of tachyarrhythmia. A device example includes an atrial sensing circuit, a ventricular sensing circuit and an atrioventricular (AV) delay adjustment circuit. The atrial sensing circuit detects a first fast atrial pace that concludes a timing interval that is shorter than or equal to a first threshold value. The ventricular sensing circuit detects a first condition that comprises a sensed intrinsic first fast ventricular contraction that occurs within a specified first period of a most recently detected first fast atrial pace. The fast ventricular contraction concludes a timing interval that is shorter than or equal to a second threshold value. The AV delay adjustment circuit attempts to decrease an AV delay at least in part in response to detecting the first condition.

A method example includes detecting a first fast atrial pace that concludes a timing interval that is shorter than or equal to a first threshold value, detecting a first condition that includes a sensed intrinsic first fast ventricular contraction occurring within a specified first period of a most recently detected first fast atrial pace that concludes a timing interval that is shorter than or equal to a second threshold value; and attempting to decrease an atrioventricular (AV) delay at least in part in response to detecting the first condition.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Figure 1:
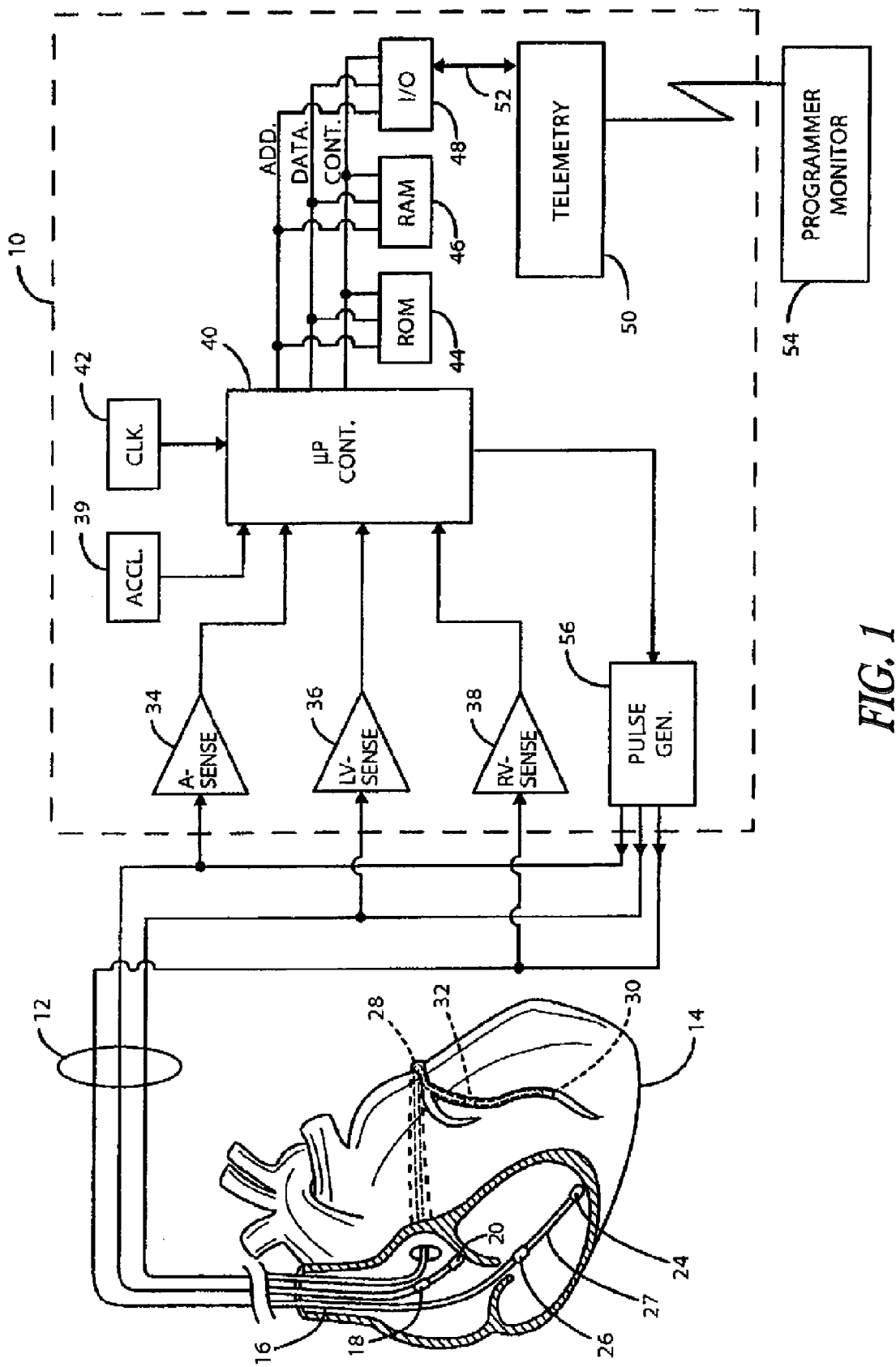
FIG. 1 is a block diagram of portions of an implantable cardiac rhythm device.

FIG. 1 is a block diagram of portions of an implantable cardiac rhythm device (CRMD 10). The CRMD 10 is shown connected to a heart 14 by one or more electrodes, which can be located on one or more leads 12. A ventricular lead 16 includes a distal tip electrode 24 and a proximal ring electrode 26 separated by insulation 27 and placed in the right ventricle (RV). An atrial lead includes a distal tip electrode 20 and a proximal ring electrode 18 placed in the right atrium (RA). An additional lead 28 is routed through the coronary sinus of the heart and from there it is routed down a selected vein on the left side of the heart so that ring electrodes 30 and 32 are positioned to sense depolarization of the left ventricle (LV).

Signals picked up by electrode 20 are applied to an atrial sense amplifier 34 forming a part of the CRMD 10. Likewise, signals from the LV lead 28 are applied to a left ventricle sense amplifier 36. Conductors in the RV lead 16 connect to the electrodes 24 and 26 and carry signals relating to depolarization of the RV to a right ventricular sense amplifier 38.

The sense amplifiers 34, 36 and 38 may include signal processing circuitry for amplifying or shaping analog signals picked up by the electrodes in and on the heart and these analog signals are applied to an analog-to-digital converter forming a part of a controller 40. Controller 40 may include a digital signal processor, application specific integrated circuit (ASIC), microprocessor, or other type of processor, interpreting or executing instructions in software or firmware. In a rate adaptive CRMD, a physiologic sensor, such as accelerometer 39, is also provided. A crystal controlled clock 42 provides timing signals to the controller 40. Also coupled to the controller 40 by an address bus (ADD), a data bus (DATA), and control bus (CONT) are a read-only memory (ROM) 44, a random access memory (RAM) 46 and an input/output interface (I/O) 48. A telemetry circuit 50 is coupled to the I/O circuit 48 by a bi-directional bus 52 and functions to allow a two-way communication with an external programmer/monitor 54.

In certain examples, the ROM memory 44 stores instructions executable by the controller 40. The executable instructions form a program which when executed by the controller 40 functions to control a pulse generator 56, such as by causing it to issue cardiac stimulating pulses over the leads 16 and 28 in order to initiate depolarization of the right atrium, the right ventricle, and the left ventricle at times determined by the controller 40.

Using the external programmer 54 and the telemetry capabilities of the CRMD 10, a medical professional can program into the CRMD 10 various operating parameters via the RAM memory 46.

In some examples, dual-chamber pacemakers allow programming of pacing modes, lower rate limits, pulse width, pulse amplitude, sensitivity, refractory periods, maximum tracking rate, AV delay and other parameters. Among pacemaker patients who are chronotropically incompetent (e.g., unable to increase sinus node rate appropriately with exercise), rate-responsive pacemakers may allow for increases in pacing rates with exercise. Appropriately adjusting a device response to exercise can be challenging. For programming rate-response capability, some CRMDs include procedures for initial programming of rate-response parameters, subsequent automatic adjustment of these parameters, and retrievable diagnostic data, via the telemetry link, to assess the appropriateness of the rate response. Rate-responsive pacemakers may require programmable features to regulate the relation between a sensor output and pacing rate and to limit the maximum sensor-driven pacing rate, i.e., the URL. These programmable parameters may need to be individually adjusted for each patient, and the choice of one programmable parameter will often depend on the availability of another parameter. For example, in a patient with complete AV block and paroxysmal atrial fibrillation, a dual-chamber pacemaker not having a mode-switching capability most appropriately would be programmed to its DDIR mode, whereas in the same patient, a pacemaker with mode-switching capability most appropriately would be programmed to its DDDR mode with mode switching.

When non-physiological atrial tachyarrhythmias, such as atrial fibrillation or flutter, occur paroxysmally in a patient with a dual-chamber pacemaker programmed to conventional DDD or DDDR mode, the tachyarrhythmia may be tracked near the programmed maximum tracking rate (MTR), leading to an undesirable acceleration of ventricular pacing rate. Some dual chamber devices detect rapid, non-physiological atrial rates and automatically switch modes to one that does not track atrial activity, such as DDI or DDIR. When the atrial tachyarrhythmia terminates, the pacemaker automatically reverts back to its DDD or DDDR mode.

Figure 2:
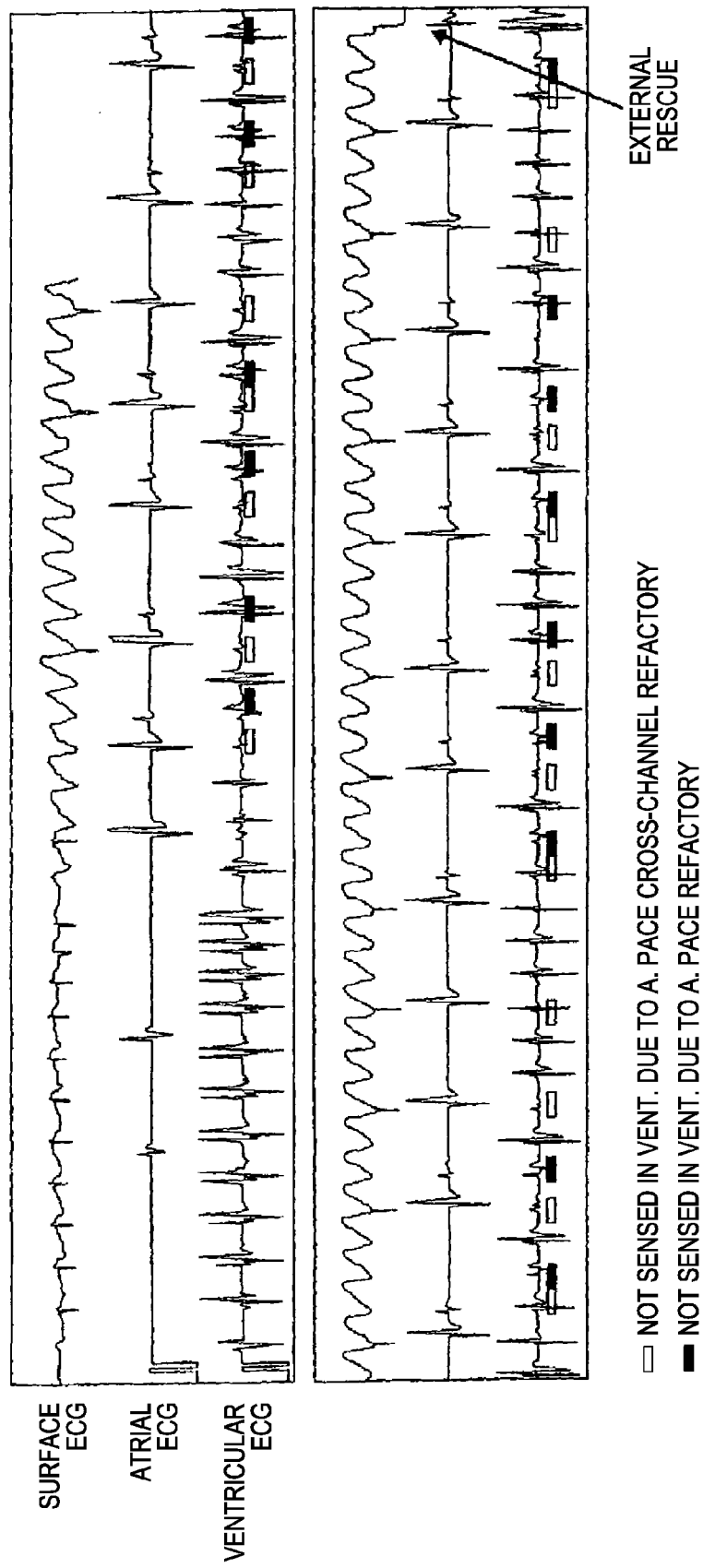
FIG. 2 shows examples of ECG waveforms.

Referring to FIG. 2, the uppermost waveform comprises a surface ECG aligned time-wise with an atrial electrocardiogram (ECG) (middle waveform) and a ventricular ECG (bottom waveform) where the subject has had an episode of ventricular tachycardia induced. The ECG signals are developed by the CRMD 10. The illustrated atrial and ventricular electrograms were produced using a pacemaker operating in the DDI mode with a LRL of 50 beats-per-minute and a URL of 120 beats-per-minute and with a fixed AV delay of 300 ms and rate smoothing down 12% and up 9%. It can be seen from this waveform that by initially pacing the subject at a high rate of about 220 beats-per-minute, an episode of ventricular tachycardia or flutter has been induced, represented by the somewhat sinusoidal-shaped waves in the surface EKG. The lower waveform has been annotated to reflect where ventricular beats were under-sensed due to A-pace cross-channel refractory and V-pace refractory conditions. Those beats that were not sensed due to A-pace cross-channel refractory (i.e., ventricular sense channel refractory periods that have been initiated by atrial pacing) are underlined with a open bar and those not sensed due to V-pace refractory are underlined with a hatched bar. The waveforms show that numerous ventricular beats have gone undetected during the aforementioned refractory periods.

Figure 3:
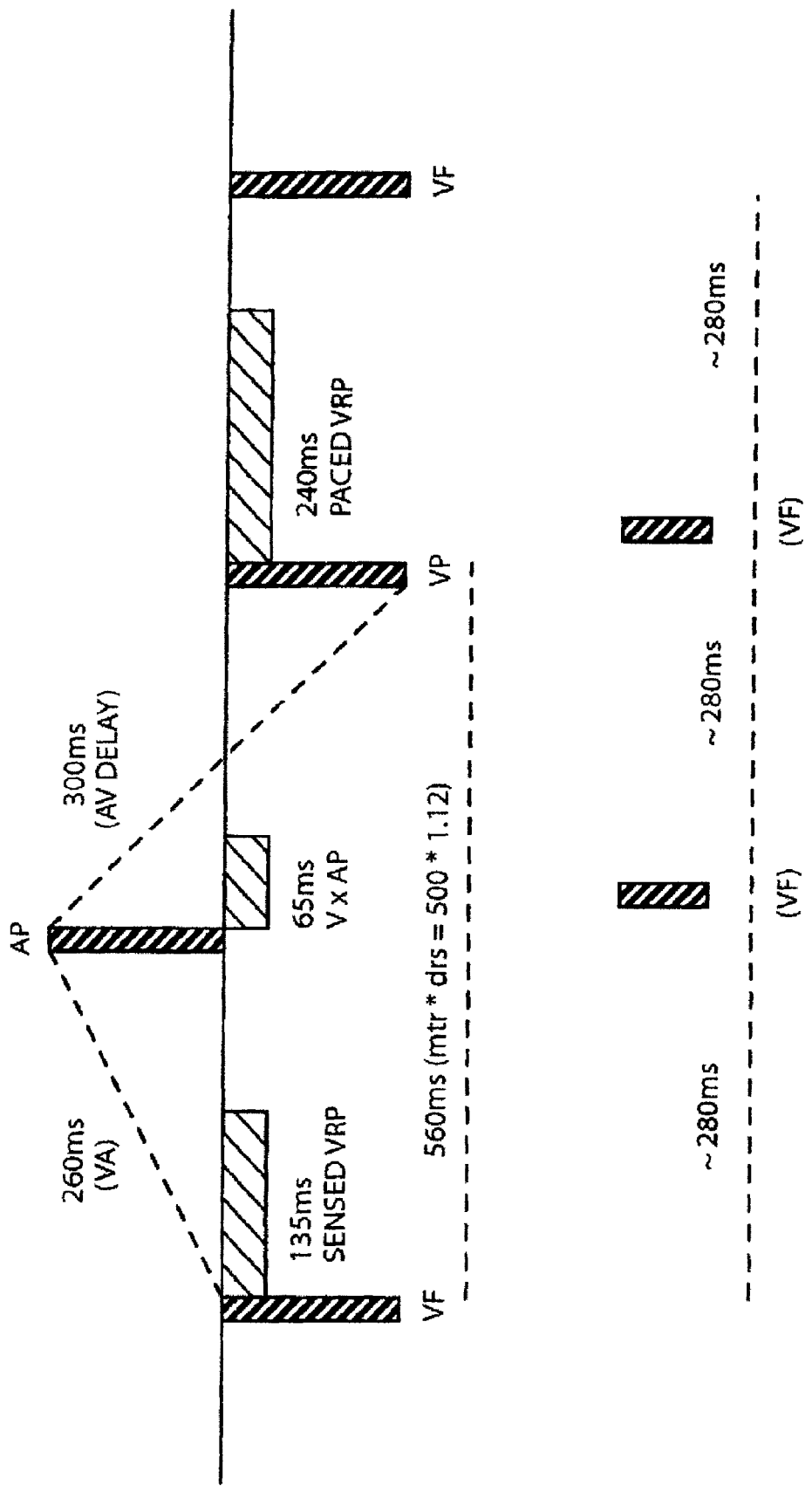
FIG. 3 is a timing diagram illustrating an example manner in which timing cycles are set up in a multi-chamber pacemaker or a pacemaker/defibrillator.

FIG. 3 is a timing diagram illustrating an example manner in which timing cycles are set up in a multi-chamber pacemaker or pacemaker/defibrillator and illustrating under-sensing because of the presence of atrial refractory periods and ventricular refractory periods in the timing cycle. Starting with a first ventricular beat VF, which stands for a ventricular fib beat, a time is established when the next ventricular pace (VP) beat will be delivered by the pacemaker. In the case illustrated, this time interval is determined by programmable variables including the "maximum tracking rate" MTR and the "down-rate smooth limit" (drs). These two factors are multiplied and with a MTR of 500 and a drs of 1.12, the time interval from the sensed beat VF to the next paced beat (VP) is 560 milliseconds.

The AV delay value, here 300 ms, is a parameter programmed in by the physician and this establishes the time of occurrence of the A-pace (AP) pulse produced by the implantable device. The diagram of FIG. 3 also shows that following the occurrence of a sensed ventricular beat, there is a fixed refractory interval of 135 ms. Likewise, following the occurrence of an A-pace signal, a preprogrammed A-pace cross-channel refractory period (here 65 ms) is provided. Finally, following a paced ventricular beat (VP), there is a ventricular refractory period whose length is also a programmable quantity, here set at 240 ms.

Referring again to FIG. 2, it will be seen that the ventricular tachycardia is at an interval of about 280 ms, which therefore causes the ventricular fibrillation beats (VF) to fall within the A-pace cross-channel refractory period and the paced ventricular refractory period. Hence, those beats are not sensed by the sense amplifiers 34, 36 or 38, which are purposely disabled at these times.

From what has been explained with the aid of FIGS. 2 and 3, if the device is pacing the heart at a rate approaching the URL and a ventricular tachyarrhythmia occurs, the detection and possible treatment of the tachyarrhythmia may be frequently delayed or completely inhibited due to under-sensing because of A-pace cross-channel refractory.

Tachyarrhythmia is sometimes categorized into three rate zones—VF, VT, and VT-1. Zone VF is for ventricular fibrillation and is the highest rate zone. Zone VT is for ventricular tachycardia. Zone VT-1 is sometimes referred to as slow tachy. A programmed interval referred to as the "lowest tachy zone interval" defines the lower boundary of the VT-1 rate zone. It is the longest interval (slowest rate) that sensed beats can have and be classified as a tachycardia. This parameter varies from patient-to-patient and is arrived at by observing ECG data for the patient over a period of time.

Figure 4:
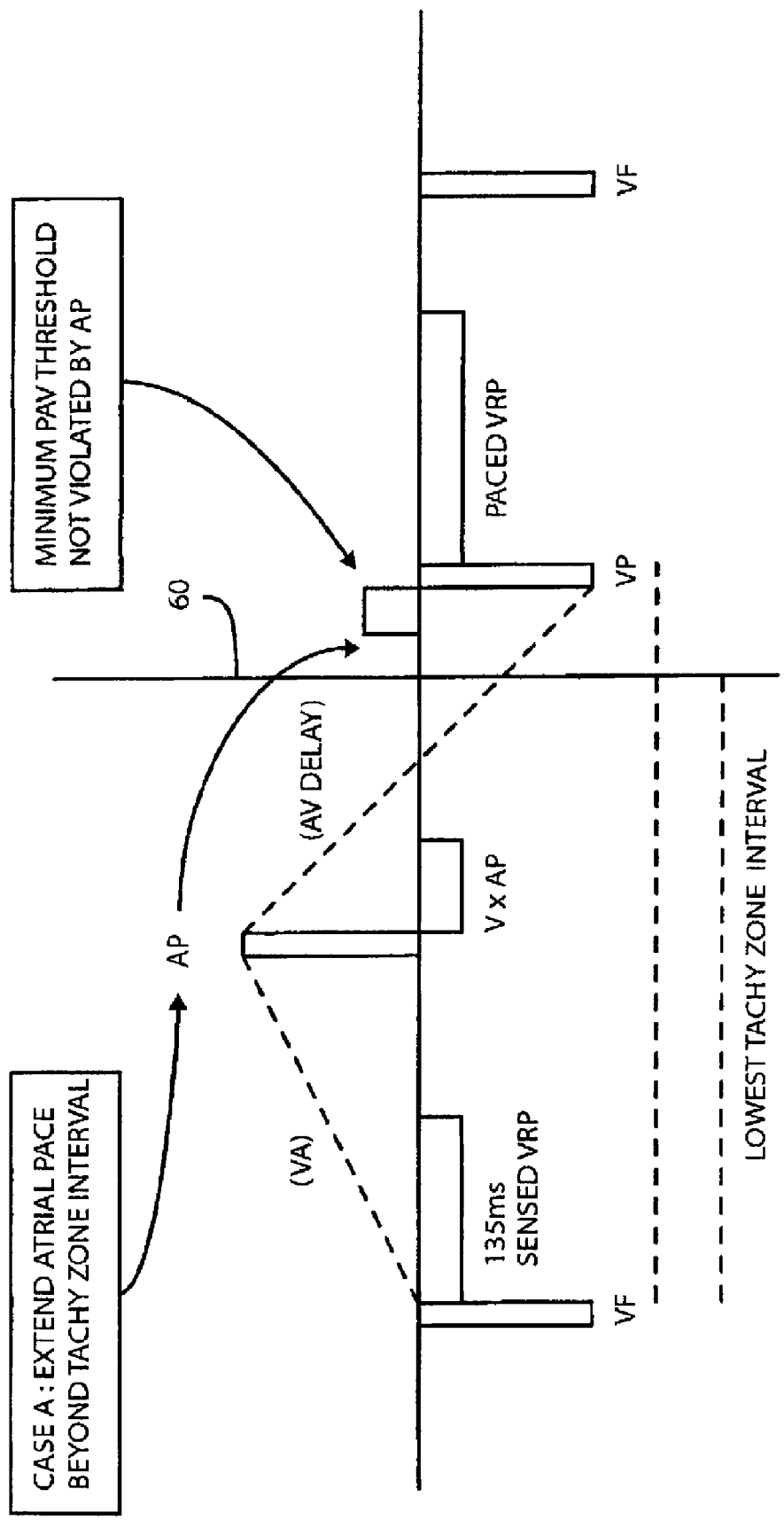
FIG. 4 is a timing diagram illustrating ventricular and atrial events and a lowest tachyarrhythmia zone interval.

The timing diagram of FIG. 4 includes a long vertical line 60 marking the lowest tachyarrhythmia zone interval. Any ventricular beats which are occurring at a rate that makes the interval between beats shorter than the lowest rate tachyarrhythmia zone rate interval are possibly indicative of a tachyarrhythmia episode. The interval between the occurrence of an atrial pace (AP) and the line 60 is a zone in which under-sensing can occur due to the atrial cross-channel refractory period that follows the AP pulse.

To avoid under-sensing, a tachyarrhythmia detection feature limits the A-V delay and limits the pacing rate. The detection feature insures that the A-pace, the V-pace and the associated refractory periods fall outside the ventricular tachyarrhythmia zones. This reduces the chance that ventricular tachyarrhythmia events will be under-sensed due to the refractory periods and enhances ventricular tachyarrhythmia detection.

In some examples, the detection feature is automatically activated when conditions for entry into the feature are satisfied. In some examples, the detection feature is only automatically activated under certain conditions. For instance, if the device is a cardiac function management (CFM) device, the CFM device may be in DDD(R) or DDI(R) pacing mode, and the pacing state of the CFM device is preferably normal, post-shock, post atrial therapy, or in anti-tachy response (ATR). The detection feature should not be activated in a user-activated temporary state such as temporary bradycardia pacing or in a user activated device test state such as a user-commanded pacing threshold test. If conditions for exiting the feature are satisfied, the feature is deactivated and no longer limits the A-V delay and pacing rate. In some examples, the detection feature is exited if the device enters a programming mode that does not support the detection feature.

Figures 5A, 5B:
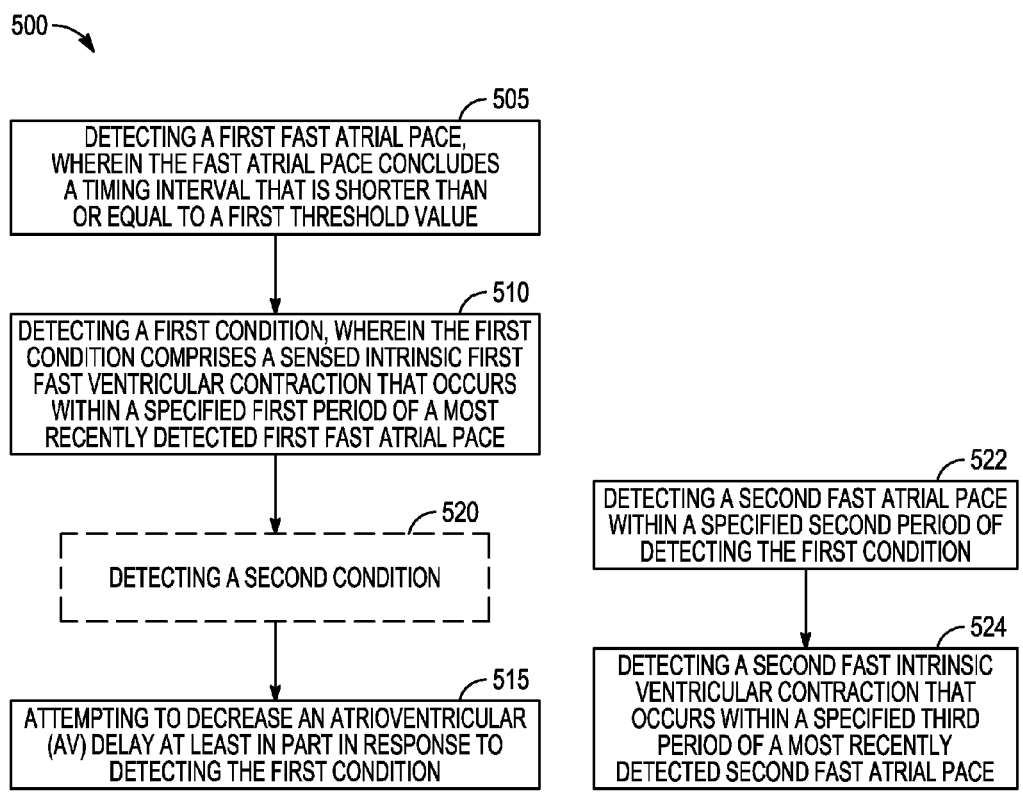
FIGS. 5A and 5B show a flow diagram of a method of adjusting A-V delay and enhancing ventricular tachyarrhythmia detection.
Figure 6:
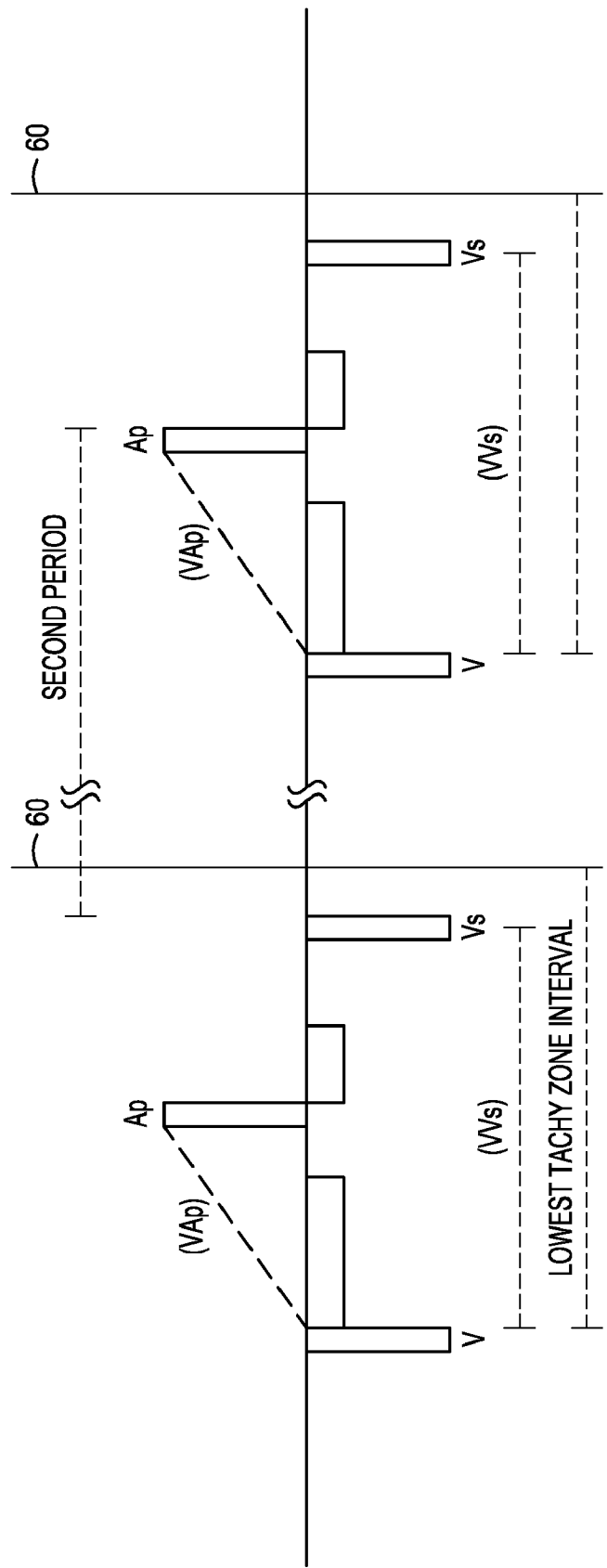
FIG. 6 illustrates an example of a fast ventricular contraction concluding a timing interval that is shorter than or equal to a second threshold value.

FIG. 5 is a flow diagram of a method 500 of adjusting A-V delay and enhancing ventricular tachyarrhythmia detection. At block 505, a first fast atrial pace is detected. The fast atrial pace concludes a timing interval that is shorter than or equal to a first threshold value. An example of a fast atrial pace is illustrated in FIG. 6. In the example, the timing interval is an interval that begins with a ventricular event (sense or pace) and ends with an atrial pace (VAp). The first threshold value is an interval that is shorter than or equal to a lowest-rate tachyarrhythmia rate interval threshold 60. The atrial pace is a fast atrial pace because the resulting VAp interval is shorter than or equal to this first threshold value.

Referring to FIG. 5, a first condition is detected at block 510. The first condition includes a sensed intrinsic first fast ventricular contraction that occurs within a specified first period of a most recently detected first fast atrial pace. The fast ventricular contraction concludes a timing interval that is shorter than or equal to a second threshold value. An example is illustrated in FIG. 6. In the example, the time interval is an interval from the ventricular event to a ventricular sense (VVs). The second threshold value is an interval (VVs) that is shorter than or equal to a lowest-rate tachyarrhythmia rate interval threshold 60. In the example illustrated, the first ventricular fast ventricular contraction (Vs) occurs within the same cardiac cycle of the fast atrial pace, but this is not necessary for the first condition to be satisfied. In some examples, the first condition is satisfied when a fast VVs interval occurs within three cardiac cycles of the fast VAp interval. In some examples, the first condition includes a fast VVs interval occurring within from two cardiac cycles to eight cardiac cycles of the fast VAp interval.

Returning to FIG. 5, at block 515, a decrease in an atrio-ventricular (AV) delay is attempted at least in part in response to detecting the first condition at block 515. If the first condition does not occur, e.g., a sensed intrinsic first fast ventricular contraction does not occur within the specified first period, the method 500 includes returning to look for a fast VAp.

In determining whether the first condition is satisfied, the number of ventricular events to time the specified period should be counted relative to the latest fast atrial pace. For example, if the specified first period is three cardiac cycles and if a second fast atrial pace occurs before the fast VVs is detected, the specified first period is three cardiac cycles after the latest fast atrial pace. In some examples, the cardiac cycle count is reset after the second fast atrial pace.

If the first condition does occur, the method 500 may include detecting a second condition at block 520 before the decrease in AV delay is attempted. The second condition follows the first condition (e.g., the second condition follows the first detected fast VVs interval). At block 522, the second condition includes detecting a second fast atrial pace within a specified second period of detecting the first condition. An example of a second condition is illustrated in FIG. 6. In the example, the second condition includes a fast atrial pace (a fast VAp interval) defined by the lowest tacharrhythmia rate zone interval 60. The specified second period includes a specified number of cardiac cycles of the first condition. In some examples, the specified second period includes the second fast VAp interval occuring within three cardiac cycles of the first fast VVs interval. In some examples, the second period includes the second fast VAp interval occurring within from two cardiac cycles to eight cardiac cycles of the first fast VVs interval.

Returning to FIG. 5, at block 524, the second condition also includes detecting a second fast intrinsic ventricular contraction (VVs) within a specified third period of a most recently detected second fast atrial pace (VAp). In some examples, the third period includes a fast VVs interval occuring within three cardiac cycles of the fast VAp interval. In some examples, the third period includes a fast VVs interval occurring within from two cardiac cycles to eight cardiac cycles of the fast VAp interval. If both the first and second conditions are detected, the method 500 includes attempting to decrease the AV delay. If the second condition does not occur (e.g., a sensed fast atrial pace does not occur within the second specified, or a sensed intrinsic first fast ventricular contraction does not occur within the specified third period), the method 500 includes returning to look for a first fast VAp at block 505.

Figure 7:
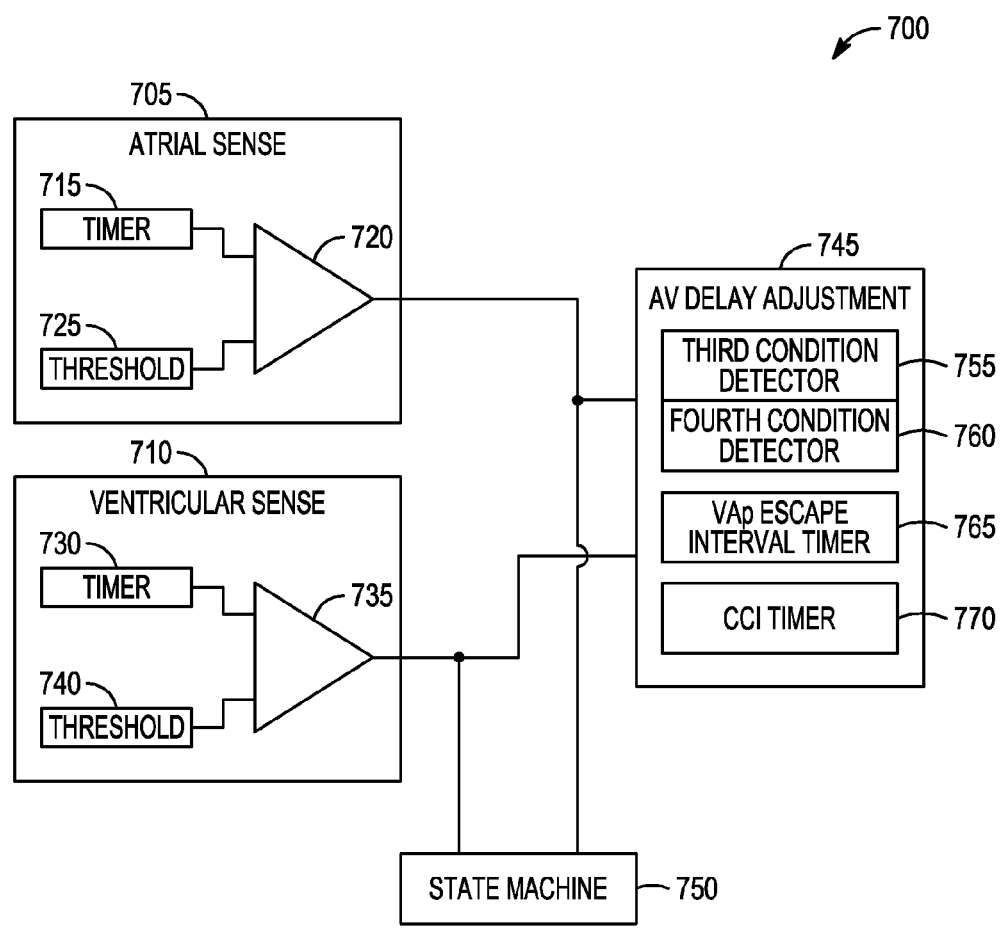
FIG. 7 shows a block diagram of portions of an apparatus to detect the first condition for attempting to adjust an atrioventricular (AV) delay.

FIG. 7 shows a block diagram of portions of an apparatus 700 to detect the first condition. In some examples, the apparatus includes a CFM device. The apparatus 700 includes an atrial sensing circuit 705 and a ventricular sensing circuit 710. The atrial sensing circuit 705 includes an atrial sensing circuit timer 715 and an atrial sensing circuit comparator 720. The atrial sensing timer 715 measures a time interval concluded by an atrial pace. The atrial sensing circuit comparator 720 includes a first input coupled to the atrial sensing circuit timer 715 and a second input coupled to receive a first threshold value 725. In certain examples, the second input is coupled to a memory circuit, such as a register for example, to receive the first threshold value. The atrial sensing circuit comparator 720 detects a first fast atrial pace. The fast atrial pace concludes a timing interval that is shorter than or equal to the first threshold value.

In some examples, the timing interval begins with a ventricular event (sense or pace) and ends with an atrial pace (VAp). The first threshold value is an interval that is shorter than or equal to a lowest-rate tachyarrhythmia rate interval threshold. The atrial sensing circuit comparator 720 detects a fast atrial pace that results in a VAp interval shorter than or equal to the lowest-rate tachyarrhythmia rate interval threshold.

The ventricular sensing circuit 710 includes a ventricular sensing circuit timer 730 and a ventricular sensing circuit comparator 735. The ventricular sensing circuit comparator 735 detects a first condition. The first condition includes a sensed intrinsic first fast ventricular contraction Vs that occurs within a specified first period of a most recently detected first fast atrial pace. In some examples, the first specified period is a specified number of cardiac cycles. The fast ventricular contraction concludes a timing interval that is shorter than or equal to a second threshold value 740. In some examples, the second threshold value is an interval (VVs) that is shorter than or equal to a lowest-rate tachyarrhythmia rate interval threshold. The apparatus 700 also includes an atrioventricular (AV) delay adjustment circuit 745. The AV delay adjustment circuit decreases an AV delay at least in part in response to detecting the first condition.

In certain examples, the apparatus 700 optionally detects the second condition. The atrial sensing circuit timer 715 and the atrial sensing circuit comparator 720 detect a second fast atrial pace within a specified second period of detecting the first condition. The second condition is declared if the ventricular sensing circuit timer 730 and the ventricular sensing circuit comparator 735 detect a second fast intrinsic ventricular contraction that occurs within a specified third period of a most recently detected second fast atrial pace. The AV delay adjustment circuit attempts to decrease the AV delay in response to detecting both the first and second conditions.

Figure 8:
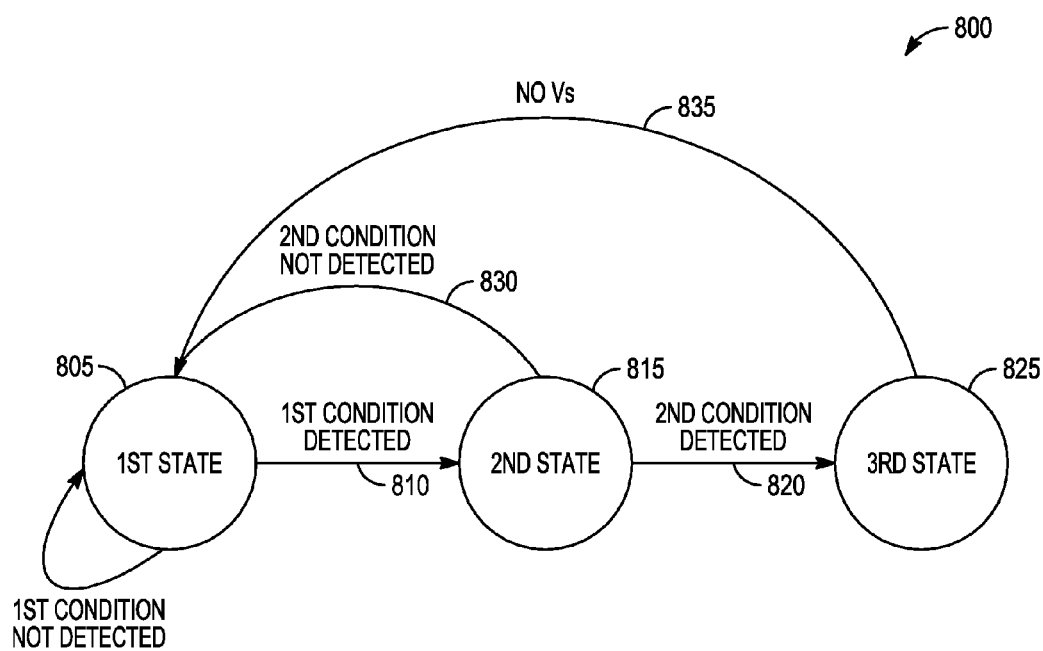
FIG. 8 shows a state diagram for a state machine.

In some examples, the apparatus 700 includes a state machine 750. The state machine 750 provides first, second, and third operating states. FIG. 8 shows a state diagram 800 for the state machine 750. In some examples, the first operating state 805 includes waiting for a fast atrial pace to be detected. The fast atrial pace concludes a timing interval that begins with a ventricular event (sense or pace), ends with an atrial pace (VAp), and is faster or equal to a first threshold interval value.

If a first condition is not detected, the state machine 750 continues at 805 waiting for the first condition. If the first condition is detected, a first trigger 810 transitions the state machine 750 from the first operating state 805 to the second operating state 815. In some examples, the first condition includes a sensed intrinsic first fast ventricular contraction (Vs) that occurs within a specified first period of a most recently detected first fast atrial pace (VAp). The first period may be specified in terms of a number of cardiac cycles. The Vs concludes a time interval from the ventricular event of the fast atrial pace to the ventricular sense (VVs). The first condition is satisfied if the VVs interval is shorter than or equal to a second threshold value, such as the lowest-rate tachyarrhythmia rate interval threshold for example.

If a second condition is detected, a second trigger 820 transitions the state machine 750 to the third operating state 825. In some examples, the second condition includes a fast atrial pace (a fast VAp interval) defined by the lowest tachyarrhythmia rate zone interval. The fast VAp interval occurs within a specified second period of the VVs interval of the first condition. The second condition also includes a second fast intrinsic ventricular contraction (VVs) that occurs within a specified third period of the most recently detected second fast atrial pace (VAp). The third operating state 825 includes attempting to decrease the AV delay.

If, while in the second operating state 815, the second condition is not detected within a specified fourth period after transitioning to the second operating state 815, a third trigger 830 transitions the state machine 750 to the first operating state 805, where the state machine 750 resumes waiting for the first condition to occur. If some cases the first part of the second condition, the fast VAp interval may be detected but not the second fast intrinsic ventricular contraction corresponding to the second VVs interval. If the second fast intrinsic ventricular contraction does not occur within a specified fifth period, a fourth trigger 835 transitions the state machine 750 to the first operating state 805.

When the state machine 750 enters the third operating state 825, the tachyarrhythmia detection feature is activated. The detection feature determines a desired current cardiac cycle interval (CCI) and a ventricular event to atrial pace interval (VAp) that enhances tachyarrhythmia detection. In some examples, a marker is stored or communicated to a second device to indicate the activation. The AV delay adjustment circuit 745 attempts to decrease the AV delay. In some examples, the AV delay adjustment circuit 745 includes a specified minimum AV delay. For example, this minimum delay may be a programmed parameter. In some examples, the AV delay adjustment circuit 745 attempts to decrease the AV delay while preserving the specified minimum AV delay.

Figure 9:
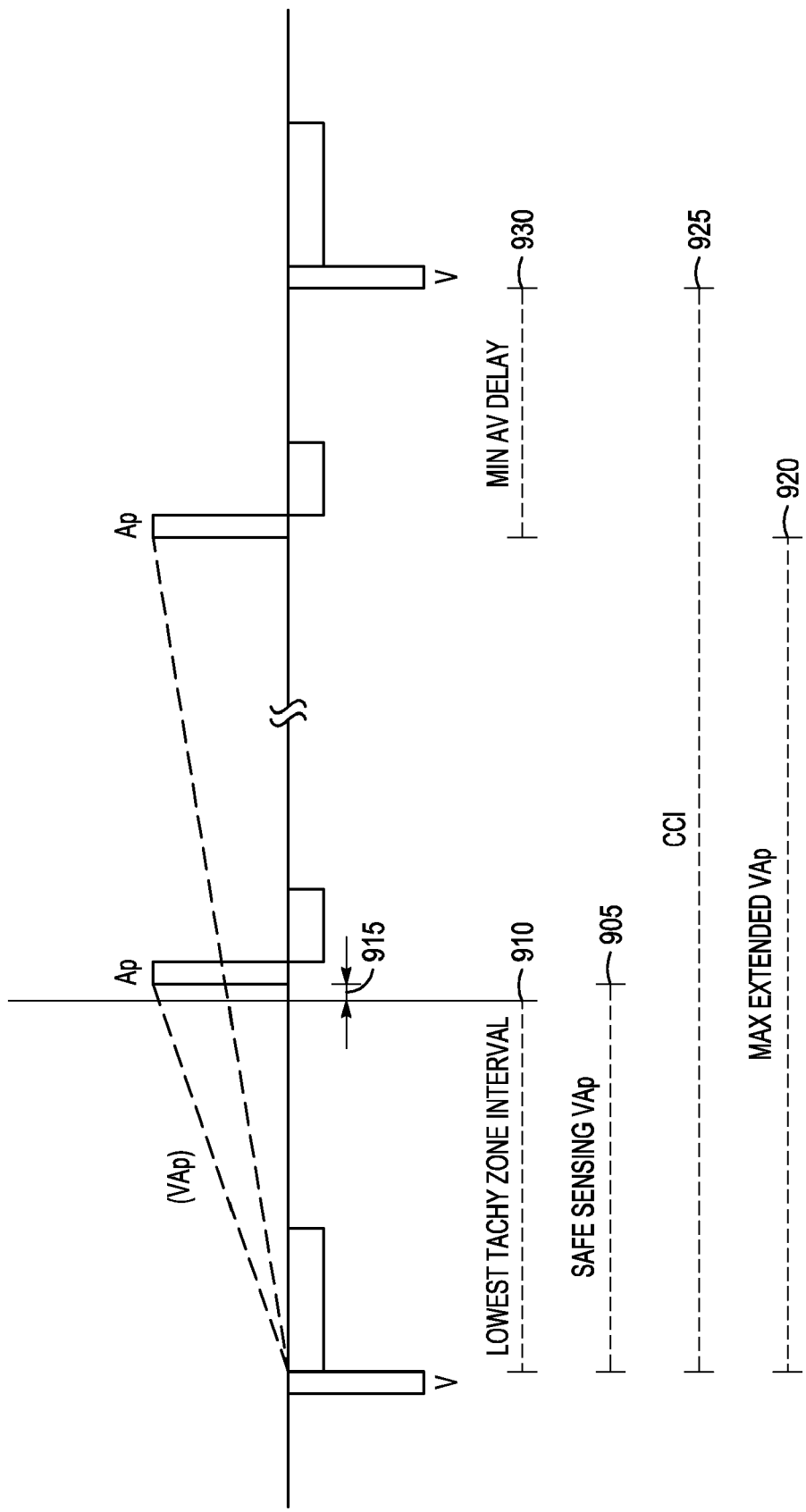
FIG. 9 shows an example illustration of AV delay intervals.

The AV delay adjustment circuit 745 determines a minimum and a maximum VAp intervals. FIG. 9 shows an example illustration of the VAp intervals. A safe sensing VAp timing interval 905 ($ss_{13}VAp$) is equal to the lowest-rate tachyarrhythmia rate interval 910 plus an incremental value 915. In some examples, the incremental value is five milliseconds (5 ms). The safe sensing VAp interval is the minimum VAp interval. A maximum extended VAp timing interval 920 ($me_{13}Vap$) is equal to a current cardiac cycle (CCI) 925 less a specified minimum AV delay 930. In some examples, the minimum AV delay is eighty milliseconds (80 ms).

Figure 10:
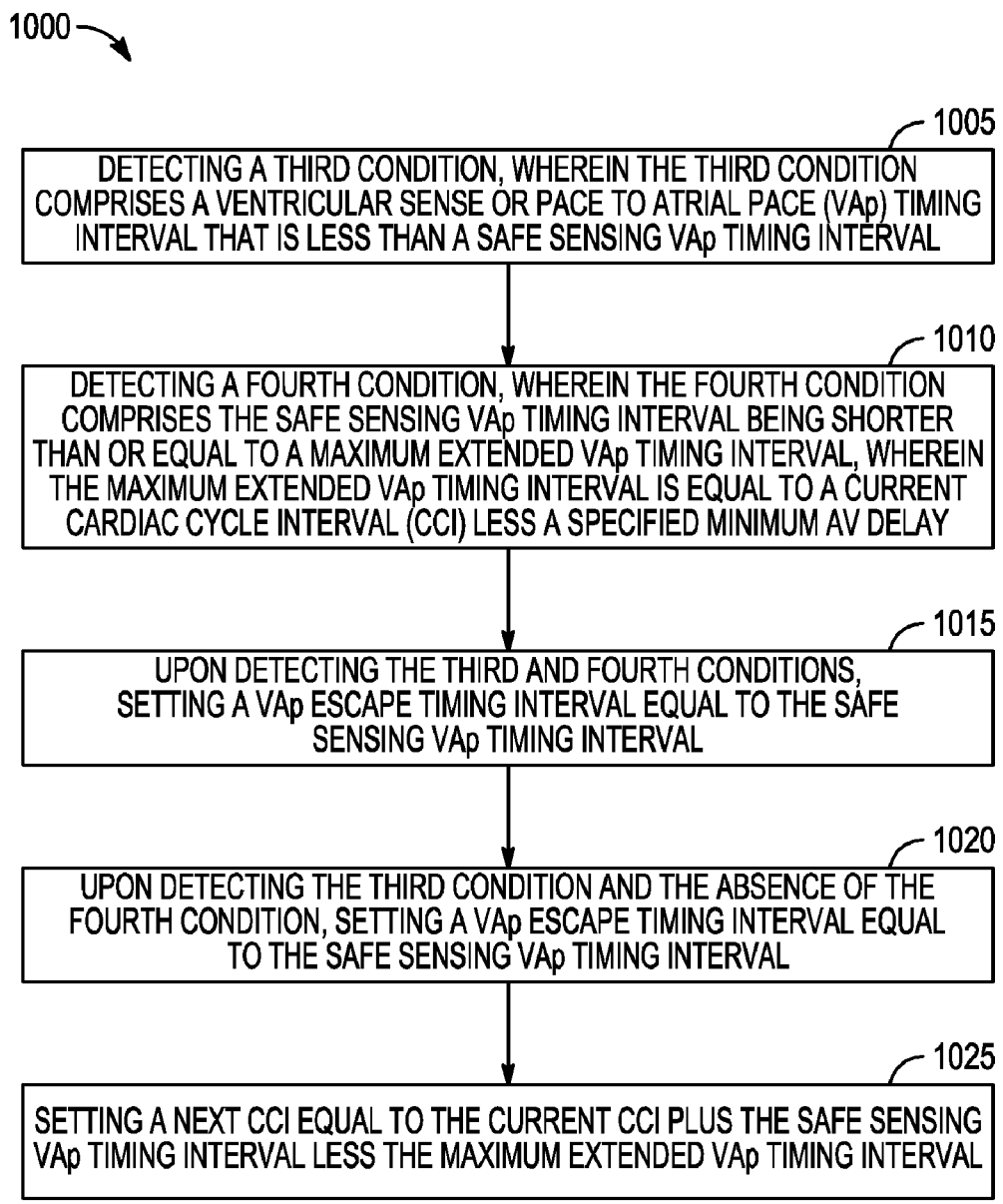
FIG. 10 is a flow diagram of a method of decreasing AV delay to enhance ventricular tachyarrhythmia detection.

FIG. 10 is a flow diagram of a method 1000 of decreasing AV delay to enhance ventricular tachyarrhythmia detection. At block 1005, a third condition is detected. The third condition includes a ventricular sense or pace to atrial pace (VAp) timing interval that is less than the safe sensing VAp timing interval.

At block 1010, a fourth condition is detected. The fourth condition includes the safe sensing VAp timing interval being shorter than or equal to the maximum extended VAp timing interval. At block 1015, a VAp escape timing interval equal is set equal to the safe sensing VAp timing interval if the third and fourth conditions are detected (i.e., $VAp=ss_{13}VAp$).

If the third condition is detected but the fourth condition is absent, at block 1020, the VAp escape timing interval is set equal to the safe sensing VAp timing interval (i.e., $VAp=ss_{13}VAp$). Additionally, at block 1025, the next CCI is set equal to the current CCI plus the safe sensing VAp timing interval less the maximum extended VAp timing interval (i.e., $CCI=CCI+(ss_{13}VAp-me_{13}VAp)$). If both the third and fourth conditions are absent, the method 1000 includes leaving the VAp escape timing interval unchanged from an existing value of the VAp escape timing interval.

Returning to FIG. 7, in some examples, the AV delay adjustment circuit 745 includes a third condition detector 755 and a fourth condition detector 760 to detect the third and fourth conditions. The AV delay adjustment circuit 745 also includes a VAp escape interval timer 765 and a CCI timer 770. The VAp escape interval timer 765 times a VAp escape interval equal to the safe sensing VAp timing interval if the third and fourth conditions are detected. If the third condition is detected but the fourth condition is not detected, the VAp escape interval timer 765 sets the VAp escape interval equal to the safe sensing VAp timing interval, and the CCI timer 770 sets the next CCI equal to the current CCI plus the the safe sensing VAp timing interval less the maximum extended VAp timing interval. If both the third and fourth conditions are absent, the VAp escape interval timer 765 leaves the VAp escape timing interval unchanged.

In some examples, the apparatus 700 may be a CFM device that provides bi-ventricular pacing. If the LV offset is programmed to be a negative value with respect to the RV offset, it may be preferable to program the LV offset to zero while the tachyarrhythmia detection feature is active. This may avoid unwanted or unintended interactions of the LV offset with the tachyarrhythmia detection feature.

In some examples, the various functions described herein can be implemented as modules. Modules can be software, hardware, firmware or any combination thereof. Multiple functions can be performed in one or more modules as desired, and the embodiments described are merely examples. The software and/or firmware are typically executed on a processor. For example, the processor may be included in the controller 40 of the CRMD 10 of FIG. 1.

In some examples, the tachyarrhythmia detection feature is exited if a number of number of consecutive slow ventricular cycles are present for a specified sixth period. In some examples, the tachyarrhythmia detection feature is exited if ten consecutive slow ventricular timing intervals are present. In some examples, a ventricular timing interval is slow if it exceeds the lowest-rate tachyarrhythmia rate interval threshold.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," ""second," and "third," etc. are used merely as labels, and are not intended to impose numerical requirements on their objects.

The Abstract is provided to comply with 37 C.F.R. §1.72 (b), which requires that it allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment.

What is claimed is:

1. A method comprising:

detecting a first fast atrial pace with an implantable medical device (IMD), wherein the fast atrial pace concludes a timing interval that is shorter than or equal to a first threshold value;

detecting a first condition, wherein the first condition comprises a sensed intrinsic first fast ventricular contraction that occurs within a specified first period of a most recently detected first fast atrial pace, wherein the fast ventricular contraction concludes a timing interval that is shorter than or equal to a second threshold value; and attempting, with the IMD, to decrease an atrioventricular (AV) delay at least in part in response to detecting the first condition, wherein attempting to decrease an AV delay includes:

establishing a safe sensing ventricular sense or pace to atrial pace interval (VAp), wherein the safe sensing VAp timing interval is equal to a lowest-rate tachyarrhythmia rate interval threshold plus a first incremental value;

setting a VAp escape timing interval equal to the safe sensing VAp timing interval, wherein said setting comprises decreasing an escape AV delay interval when detecting a VAp that is less than the safe sensing VAp interval; and calculating a ventricular sense or pace to ventricular pace interval (VVp), wherein if said calculated ventricular sense or pace to ventricular pace interval less the lowest-rate tachyarrhythmia rate interval threshold is less than a specified fixed minimum paced AV delay interval, then delaying generation of the ventricular pace pulse until after the minimum paced AV delay interval elapses following the safe sensing VAp timing interval.

2. The method of claim 1, comprising:

detecting a second condition, wherein the second condition comprises:

detecting a second fast atrial pace within a specified second period of detecting the first condition; and detecting a second fast intrinsic ventricular contraction that occurs within a specified third period of a most recently detected second fast atrial pace; and wherein the attempting to decrease the AV delay comprises attempting to decrease the AV delay in response to detecting both the first and second conditions.

3. The method of claim 2, wherein the attempting to decrease the AV delay comprises preserving the specified minimum paced AV delay.

4. The method of claim 2, comprising:
providing first, second, and third operating states;
transitioning from the first operating state to the second operating state in response to detecting the first condition;
transitioning from the second operating state to the third operating state in response to detecting the second condition, and wherein the attempting to decrease the AV delay is performed in the third operating state;
transitioning from the second operating state to the first operating state in response to not detecting the second condition within a specified fourth period of transitioning into the second operating state; and
transitioning from the third operating state to the first operating state in response to not detecting any fast intrinsic ventricular contractions within a specified fifth period of transitioning into the third operating state.

5. The method of claim 4, wherein the attempting to decrease an atrioventricular (AV) delay in the third operating state comprises:
the detecting that the VAp timing interval is less than the safe sensing VAp timing interval, wherein the detecting comprises a third condition;
detecting a fourth condition, wherein the fourth condition comprises the safe sensing VAp timing interval being shorter than or equal to a maximum extended VAp timing interval, wherein the maximum extended VAp timing interval is equal to a current cardiac cycle interval (CCI) less a specified minimum AV delay; and
wherein setting the VAp escape timing interval equal to the safe sensing VAp timing interval includes setting the VAp escape interval equal to the safe sensing VAp timing interval upon detecting both the third and fourth conditions.

6. The method of claim 5, wherein upon detecting the third condition and the absence of the fourth condition:
setting the VAp escape timing interval equal to the safe sensing VAp timing interval; and
setting a next CCI equal to the current CCI plus the safe sensing VAp timing interval less the maximum extended VAp timing interval.

7. The method of claim 5, wherein upon detecting the absence of the third and fourth conditions, leaving the VAp escape timing interval unchanged from an existing value of the VAp escape timing interval.

8. The method of claim 1, wherein the fast atrial pace concludes a ventricular sense or pace to atrial pace (VAp) timing interval, wherein the VAp timing interval is shorter than or equal to the first threshold value.

9. The method of claim 8, wherein the first threshold value is shorter than or equal to a lowest-rate tachyarrhythmia rate interval threshold.

10. The method of claim 1, wherein the first condition comprises a sensed intrinsic first fast ventricular contraction that occurs within a specified first period of a most recently detected first fast atrial pace, wherein the specified first period includes a range of two and eight cardiac cycles from the first fast atrial pace.

11. The method of claim 10, wherein the specified first period is three cardiac cycles.

12. The method of claim 1, wherein the fast ventricular contraction concludes a ventricular sense or pace to ventricular sense (VVs) timing interval that is shorter than or equal to the second threshold value.

13. The method of claim 12, wherein the second threshold value is shorter than or equal to a lowest-rate tachyarrhythmia rate interval threshold.

14. The method of claim 2, wherein the attempting to decrease an atrioventricular (AV) delay comprises:
detecting a third condition, wherein the third condition comprises the ventricular sense or pace to atrial pace (VAp) timing interval that is less than the safe sensing VAp timing interval;
detecting a fourth condition, wherein the fourth condition comprises the safe sensing VAp timing interval being shorter than or equal to a maximum extended VAp timing interval, wherein the maximum extended VAp timing interval is equal to a current cardiac cycle interval (CCI) less a specified minimum AV delay; and
upon detecting the third and fourth conditions, setting the VAp escape timing interval equal to the safe sensing VAp timing interval.

15. The method of claim 14, wherein upon detecting the third condition and the absence of the fourth condition:
setting the VAp escape timing interval equal to the safe sensing VAp timing interval; and
setting a next CCI equal to the current CCI plus the safe sensing VAp timing interval less the maximum extended VAp timing interval.

16. The method of claim 14, wherein upon detecting the absence of the third and fourth conditions, leaving the VAp escape timing interval unchanged from an existing value of the VAp escape timing interval.

17. An apparatus comprising:
means for detecting a first fast atrial pace, wherein the fast atrial pace concludes a timing interval that is shorter than or equal to a first threshold value;
means for detecting a first condition, wherein the first condition comprises a sensed intrinsic first fast ventricular contraction that occurs within a specified first period of a most recently detected first fast atrial pace, wherein the fast ventricular contraction concludes a timing interval that is shorter than or equal to a second threshold value; and
means for attempting to decrease an atrioventricular (AV) delay at least in part in response to detecting the first condition, including:
means for establishing a safe sensing ventricular sense or pace to atrial pace interval (VAp), wherein the safe sensing VAp timing interval is equal to a lowest-rate tachyarrhythmia rate interval threshold plus a first incremental value;
means for setting a VAp escape timing interval equal to the safe sensing VAp timing interval, wherein said setting comprises decreasing an escape AV delay when detecting a VAp that is less than the safe sensing VAp interval;
means for calculating a ventricular pace or sense to ventricular pace interval (VVp); and
means for delaying generation of the ventricular pace pulse until after the minimum paced AV delay interval elapses following the safe sensing VAp timing interval when said calculated ventricular sense or pace to ventricular pace interval less the lowest-rate tachyarrhythmia rate interval threshold is less than a specified minimum paced AV delay.

18. The apparatus of claim 17, comprising:
means for detecting a second condition, wherein the second condition comprises:
  detecting a second fast atrial pace within a specified second period of detecting the first condition; and
  detecting a second fast intrinsic ventricular contraction that occurs within a specified third period of a most recently detected second fast atrial pace; and
wherein the means for attempting to decrease the AV delay comprises means for attempting to decrease the AV delay in response to detecting both the first and second conditions.

19. An apparatus comprising:
an atrial sensing circuit, including:
  an atrial sensing circuit timer, configured to measure a time interval concluded by an atrial pace; and
  an atrial sensing circuit comparator, including a first input coupled to the atrial sensing circuit timer and a second input coupled to receive a first threshold value, the comparator configured to detect a first fast atrial pace, wherein the fast atrial pace concludes a timing interval that is shorter than or equal to the first threshold value;
a ventricular sensing circuit, including a ventricular sensing circuit timer and a ventricular sensing circuit comparator configured to detect a first condition, wherein the first condition comprises a sensed intrinsic first fast ventricular contraction that occurs within a specified first period of a most recently detected first fast atrial pace, wherein the fast ventricular contraction concludes a timing interval that is shorter than or equal to a second threshold value; and
an atrioventricular (AV) delay adjustment circuit, configured to, at least in part in response to detecting the first condition,
  establish a safe sensing ventricular sense or pace to atrial pace interval (VAp), wherein the safe sensing VAp timing interval is equal to a lowest-rate tachyarrhythmia rate interval threshold plus a first incremental value;
  decrease an escape AV delay, when detecting a VAp that is less than the safe sensing VAp interval, in order to set a VAp escape timing interval equal to the safe sensing VAp timing interval; and
  calculate a ventricular sense or pace to ventricular pace interval (VVp), wherein if said calculated ventricular sense or pace to ventricular pace interval less the lowest-rate tachyarrhythmia rate interval threshold is less than a specified minimum paced AV delay, then delay generation of the ventricular pace pulse until after the minimum paced AV delay interval elapses following the safe sensing VAp timing interval.

20. The apparatus of claim 19, configured to detect a second condition, the apparatus comprising:
the atrial sensing circuit timer and the atrial sensing circuit comparator configured to detect a second fast atrial pace within a specified second period of detecting the first condition; and
the ventricular sensing circuit timer and the ventricular sensing circuit comparator configured to detect a second fast intrinsic ventricular contraction that occurs within a specified third period of a most recently detected second fast atrial pace to declare the second condition; and
wherein the AV delay adjustment circuit is configured to attempt to decrease the AV delay in response to detecting both the first and second conditions.

21. The apparatus of claim 20, wherein the AV delay adjustment circuit is configured to attempt to decrease the AV delay to preserve the specified minimum paced AV delay.

22. The apparatus of claim 20, comprising:
a state machine providing first, second, and third operating states;
a first trigger for transitioning from the first operating state to the second operating state in response to detecting the first condition;
a second trigger for transitioning from the second operating state to the third operating state in response to detecting the second condition, and wherein the attempting to decrease the AV delay is performed in the third operating state;
a third trigger for transitioning from the second operating state to the first operating state in response to not detecting the second condition within a specified fourth period of transitioning into the second operating state; and
a fourth trigger for transitioning from the third operating state to the first operating state in response to not detecting any fast intrinsic ventricular contractions within a specified fifth period of transitioning into the third operating state.

23. The apparatus of claim 22, wherein the AV delay adjustment circuit is configured to attempt to decrease an atrioventricular (AV) delay in the third operating state, and wherein the AV delay adjustment circuit comprises:
a third condition detector, configured to detect a third condition that comprises the ventricular sense or pace to atrial pace (VAp) timing interval that is less than the safe sensing VAp timing interval;
a fourth condition detector, configured to detect a fourth condition that comprises the safe sensing VAp timing interval being shorter than or equal to a maximum extended VAp timing interval, wherein the maximum extended VAp timing interval is equal to a current cardiac cycle interval (CCI) less a specified minimum AV delay; and
a VAp escape interval timer, configured such that, upon detecting the third and fourth conditions, a VAp escape timing interval is set equal to the safe sensing VAp timing interval.

24. The apparatus of claim 23, wherein the VAp interval timer is configured such that upon detecting the third condition and the absence of the fourth condition:
the VAp escape timing interval is set equal to the safe sensing VAp timing interval; and comprising
a CCI interval timer configured such that a next CCI is set equal to the current CCI plus the safe sensing VAp timing interval less the maximum extended VAp timing interval.

25. The apparatus of claim 23, wherein the VAp interval timer is configured such that upon detecting the absence of the third and fourth conditions, the VAp escape interval is left unchanged from an existing value of the VAp escape timing interval.

26. The apparatus of claim 19, wherein the atrial sensing circuit timer is configured to detect a fast atrial pace that concludes a ventricular sense or pace to atrial pace (VAp) timing interval, wherein the VAp timing interval is shorter than or equal to the first threshold value.

27. The apparatus of claim 26, wherein the first threshold value is shorter than or equal to a lowest-rate tachyarrhythmia rate interval threshold.

28. The apparatus of claim 19, wherein the first condition comprises a sensed intrinsic first fast ventricular contraction that occurs within a specified first period of most recently detected first fast atrial pace, wherein the specified first period includes a range of two and eight cardiac cycles from the first fast atrial pace.

29. The apparatus of claim 28, wherein the specified first period is three cardiac cycles.

30. The apparatus of claim 19, comprising a ventricular sense or pace to ventricular sense (VVs) interval timer, and wherein the fast ventricular contraction concludes a VVs timing interval that is shorter than or equal to the second threshold value.

31. The apparatus of claim 30, wherein the second threshold value is shorter than or equal to a lowest-rate tachyarrhythmia rate interval threshold.

32. The apparatus of claim 20, wherein the AV delay adjustment circuit comprises:
   a third condition detector, configured to detect a third condition that comprises the ventricular sense or pace to atrial pace (VAp) timing interval being less than the safe sensing VAp timing interval;
   a fourth condition detector, configured to detect a fourth condition that comprises the safe sensing VAp timing interval being shorter than or equal to a maximum extended VAp timing interval, wherein the maximum extended VAp timing interval is equal to a current cardiac cycle interval (CCI) less a specified minimum AV delay; and
   a VAp escape interval timer, configured such that, upon detecting the third and fourth conditions, a VAp escape timing interval is set equal to the safe sensing VAp timing interval.

33. The apparatus of claim 32, configured such that upon detecting the third condition and the absence of the fourth condition:
   the VAp escape interval timer sets the VAp escape timing interval equal to the safe sensing VAp timing interval; and
   a CCI timer sets a next CCI equal to the current CCI plus the safe sensing VAp timing interval less the maximum extended VAp timing interval.

34. The apparatus of claim 32, configured such that upon detecting the absence of the third and fourth conditions, the VAp escape interval timer leaves the VAp escape timing interval unchanged from an existing value of the VAp escape timing interval.

* * * * *